(12) United States Patent
Kang

(10) Patent No.: US 12,011,586 B1
(45) Date of Patent: Jun. 18, 2024

(54) TIP FOR HIGH-FREQUENCY SKIN TREATMENT APPARATUS IRRADIATING UNIFORM RADIO FREQUENCY (RF)

(71) Applicant: SHENB Co., Ltd., Seoul (KR)

(72) Inventor: Sun Young Kang, Seoul (KR)

(73) Assignee: SHENB Co., Ltd., Seoul (KR)

( * ) Notice: Subject to any disclaimer, the term of this patent is extended or adjusted under 35 U.S.C. 154(b) by 0 days.

(21) Appl. No.: 18/342,840

(22) Filed: Jun. 28, 2023

(30) Foreign Application Priority Data

Dec. 26, 2022 (KR) ........................ 10-2022-0183911

(51) Int. Cl.
*A61B 18/14* (2006.01)
*A61N 1/06* (2006.01)
*A61N 1/32* (2006.01)

(52) U.S. Cl.
CPC ............... *A61N 1/06* (2013.01); *A61N 1/328* (2013.01)

(58) Field of Classification Search
CPC .......... A61B 2018/00452; A61B 2018/00458; A61B 2018/00464; A61B 2018/0047; A61B 2018/0476; A61B 2018/1475; A61B 2018/1465; A61B 2018/143; A61N 1/06; A61N 1/328
USPC .......... 606/41, 42, 49; 607/98, 99, 101, 108, 607/115
See application file for complete search history.

(56) References Cited

U.S. PATENT DOCUMENTS

| | | | |
|---|---|---|---|
| 7,479,019 B2 * | 1/2009 | Kent ........................ | H05K 1/02 439/633 |
| 8,700,176 B2 * | 4/2014 | Azar ...................... | A61B 18/14 607/101 |
| 9,474,893 B2 | 10/2016 | Lee | |
| 9,629,991 B1 * | 4/2017 | O'Brien, III ............. | A61N 1/40 |

FOREIGN PATENT DOCUMENTS

| | | |
|---|---|---|
| KR | 10-1297791 B1 | 8/2013 |
| KR | 10-1503081 B1 | 3/2015 |
| KR | 10-2438033 B1 | 8/2022 |
| KR | 10-2022-0124307 A | 9/2022 |

* cited by examiner

*Primary Examiner* — Thomas A Giuliani
(74) *Attorney, Agent, or Firm* — NSIP Law

(57) ABSTRACT

The present disclosure relates to a tip for a high-frequency skin treatment apparatus irradiating uniform radio frequency (RF), the tip being coupled to a handpiece to radiate a radio frequency (RF) signal to a human body in a non-invasive way, and comprising: a housing; a contact portion coupled to the housing and comprising a plurality of contact pins that come into close contact with skin of the human body to irradiate the skin with the RF signal; and a driver configured to drive the contact portion so that the contract portion radiates the RF signal according to a control signal transferred from the handpiece. Each of the contact pins comprises: a fixed frame; a moving frame; and an elastic body. The elastic body connects an upper inner surface of the fixed frame to an upper inner surface of the moving frame.

6 Claims, 9 Drawing Sheets

1

TIP FOR HIGH-FREQUENCY SKIN TREATMENT APPARATUS IRRADIATING UNIFORM RADIO FREQUENCY (RF)

CROSS-REFERENCE TO RELATED APPLICATIONS

This application claims priority to Korean Patent Application No. 2022-0183911, filed on Dec. 26, 2022, the entire contents of which are incorporated herein by reference.

TECHNICAL FIELD

The present disclosure relates to a tip for a high-frequency skin treatment apparatus that can uniformly perform non-invasive radio frequency (RF) irradiation, adaptively to different curvatures of the skin for each subject under treatment. More particularly, the present disclosure relates to a tip for a high-frequency skin treatment apparatus capable of uniform RF irradiation, which allows contact pins for radiating an RF signal to come into close contact with skin in spite of the curvature of the skin and to irradiate the skin with the RF signal so that a uniform RF signal is irradiated per area, thereby achieving skin treatment effects while resolving problems caused an existing non-invasive RF irradiation method or apparatus due to the skin curvature.

BACKGROUND

Recently, interest in skin treatment apparatuses or method for skin treatment or regeneration, as well as treatment of diseases or a human body, is continuously increasing with the development of medicine and medical apparatuses.

Among them, Botox, fillers, or thread lifting is used to improve skin elasticity and wrinkles, but there are certain defects such as an uncomfortable sensation in the skin or thread breakage. So, skin treatment using radio frequency (RF) irradiation for regeneration and regrowth of collagen in the skin is drawing attention.

Skin care apparatuses utilizing collagen regeneration by irradiating skin with an RF signal are classified into an invasive type and a non-invasive type depending on the treatment method used therein. In the case of the invasive manner, a needle (s) penetrates the treatment area of the human body to cause problems, such as relatively severe pain, needle marks, and difficulty of daily life, and, thus, treatment apparatuses of the non-invasive type are becoming increasingly popular.

As an example of a technology related to a treatment apparatus through non-invasive RF irradiation, Korean Laid-open Patent Publication No. 10-2022-0124307 discloses a "Complex Skin Treatment Apparatus Using a High Intensity Focused Ultrasonic Signal."

According to the prior art apparatus disclosed in the above document, it is possible to perform a treatment on a subcutaneous layer of a skin using a focused ultrasound signal. Here, a skin contact portion 200 that outputs a high-intensity focused ultrasound signal to the skin of a user has a flat surface which comes into contact with the skin, in a same manner as in the case of existing non-invasive RF signal irradiation treatment apparatuses in which the surface of the portion that comes in contact with the skin and irradiates the skin with an RF signal is made flat as can be seen in FIG. 8.

However, even when the tip of the treatment apparatus comes into close contact with the skin and irradiates the skin with an RF signal, the tip will make such contact with the skin surface in a tangential direction. Therefore, the RF irradiation and focusing position will vary depending on the surface curvature of each treatment area.

For example, as indicated in FIG. 9, when a certain area of skin is irradiated with an RF signal using a skin treatment apparatus, an area A is brought into close contact with the tip, but an area B is not brought into close contact with the tip due to the slope of the area B. As are result, the focusing depths of the two areas are different, thereby causing a problem that it is difficult to achieve the same level of skin improvement effects due to different amounts of RF irradiation.

In particular, if the curvature of the skin surface causes the focusing depth of the RF irradiation applied to the skin to be different from the focusing depth intended by an operator of the apparatus, the area B may be burned or the person being treated may suffer pain, and it is difficult to achieve the skin improvement effects desired by the operator.

Further, if the tip of the skin treatment apparatus is brought into close contact with the entire area of the skin of the person under treatment in order to solve the above problem, the tip needs to be excessively pressed by the height difference H between a height of the area A and the area B, thereby causing another problem that the person under treatment may feel uncomfortable or painful during the treatment, to make the operation of the treatment difficult.

SUMMARY

Problems to Be Resolved by the Invention

The present disclosure is made to solve the above-described problems, and an objective of the present disclosure is to provide a tip for a high-frequency skin treatment apparatus capable of uniform RF irradiation, which allows contact pins for radiating an RF signal to come into close contact with skin in spite of the curvature of the skin and to irradiate the skin with the RF signal so that a uniform RF signal is irradiated per area, thereby achieving skin treatment effects while resolving problems caused an existing non-invasive RF irradiation method or apparatus due to the skin curvature.

Another objective of the present disclosure is to provide a tip for a high-frequency skin treatment apparatus capable of uniform RF irradiation in which a plurality of contact pins formed on one surface of the tip are adaptively deformed to conform to the curvature of skin surface so that uniform contact with a human body surface is possible, and the contact pins in close contact with the skin can maintain uniform contact positions and perform uniform RF irradiation with a uniform amount of energy per area, thereby obtaining effective and efficient skin treatment and improvement effects.

Yet another objective of the present invention is to provide a tip for a high-frequency skin treatment apparatus capable of uniform RF irradiation in which the height of a pin (s) coming into close contact with the skin is automatically adjusted by an elastic force according to the curvature of the skin, and a person being treated is not subjected to excessive pressure by the contact with the tip and does not feel uncomfortable sensation caused by the contact pins, thereby enabling smooth skin treatment.

The problems to be solved by the present disclosure are not limited to the problems mentioned above, and other problems not mentioned here will be clearly understood by those skilled in the art from the description below.

Means for Solving the Problems

In order to solve the above problems, the present disclosure provides a tip coupled to a handpiece to radiate RF signal in a non-invasive way.

The tip may include a housing; a contact portion coupled to the housing and including a plurality of contact pins that come into close contact with skin of the human body to irradiate the skin with the RF signal; and a driver configured to drive the contact portion so that the contract portion radiates the RF signal according to a control signal transferred from the handpiece, wherein each of the contact pins includes: a fixed frame, an upper end of which is inserted into the housing and fixed thereto; a movable frame coupled to the fixed frame such that the movable frame is inserted into the fixed frame from a lower end of the fixed frame, the movable frame being movable in a vertical direction; and an elastic body included inside the fixed frame and the movable frame, to be compressed or extended according to an external force received by the movable frame to thereby move the movable frame, wherein the elastic body connects an upper inner surface of the fixed frame to an upper inner surface of the movable frame to prevent the movable frame from deviating from the lower end of the fixed frame.

Further, the housing may include an outer frame coupled to the handpiece; engagement members, each of which are formed at two opposing sides of the outer frame and engaged with the handpiece, so as to engage and fix the outer frame to the handpiece; and engagement holes, each of which are formed at said two opposing sides of the outer frame, such that the engagement members are inserted into the engagement holes and coupled and fixed thereto.

In addition, the housing may further include an engagement bracket; and the engagement bracket is installed into the outer frame and is coupled to one end of each of the engagement members inserted into the outer frame, such that the engagement members protrude outside of the outer frame in a state in which the engagement members are coupled to the engagement bracket.

Moreover, the elastic body may have a spring shape with an elastic restoring force.

Furthermore, the elastic body may connect an upper inner surface of the fixed frame to an upper inner surface of the movable frame to prevent the movable frame from deviating from the lower end of the fixed frame.

Also, the contact portion may further include a guide plate configured to close an open lower surface of the outer frame and being coupled to the contact pins; the guide plate includes a plurality of through-holes therein, the through-holes being formed by perforation and being spaced apart from each other in vertical and horizontal directions at regular intervals, and the plurality of contact pins passing through the through-holes; and an inner diameter of the through-holes is equal to an outer diameter of the contact pins, so that the contact pins pass through the through-holes to be inserted and fixed.

Further, the driver may include a first PCB connected to the handpiece and configured to receive the control signal; a second PCB included below the first PCB and connected to the contact pins; and signal transfer pins having two opposing ends, the two opposing ends respectively passing through the first PCB and the second PCB, to communicate signals between the first PCB and the second PCB.

In this case, a fitting member, which passes through the second PCB and is fitted and fixed thereto, is formed at the upper end of the fixed frame; the second PCB includes fitting holes therein, the fitting holes being formed by perforation and having the same diameter as the outer diameter of the fitting member; and the number of the fitting holes is equal to the number of the plurality of contact pins, and the fitting holes are spaced apart from each other at regular intervals in vertical and horizontal directions in the second PCB.

Additionally, a mounting member is formed on an inner surface of the outer frame, and the mounting member includes a first mounting member extending downward along the inner surface of the outer frame so that an upper end of the first mounting member is located on a same horizontal line as a lower surface of the first PCB, and a second mounting member extending downward along the inner surface of the outer frame so that an upper end of the second mounting member is located on a same horizontal line as a lower surface of the second PCB; and the upper end of the first mounting member comes into close contact with the lower surface of the first PCB to support the first PCB, and the upper end of the second mounting member comes into close contact with the lower surface of the second PCB to support the second PCB.

Effect of the Invention

According to the present disclosure, the contact pins for radiating an RF signal can come into uniform and close contact with the skin regardless of the curvature of the skin and irradiate the skin with the RF signal. Thus, uniform RF irradiation can be performed for the entire area of the skin, thereby achieving skin treatment effects and solving problems caused by the skin curvature in an existing non-invasive RF irradiation method or apparatus.

In addition, the plurality of contact pins formed on one surface of the tip are adaptively deformed to conform to the curvature of the skin to enable uniform contact with the surface of a human body, and the contact pins that are in close contact with the skin have uniform contact positions and perform uniform RF irradiation with a uniform amount of energy per area, thereby achieving effective and efficient skin treatment and skin care improvement effects.

Further, the height of the pin that comes into close contact with the skin is automatically adjusted according to the curvature of the skin by the elastic force, and a person under treatment does not feel excessive pressure from the contact with the tip or uncomfortable sensation caused by the contact pins, thus enabling smooth skin treatment operation.

Effects of the present invention are not limited to the effects mentioned above, and other effects not mentioned here will be clearly understood by those skilled in the art from the description below.

DETAILED DESCRIPTION

Figure 1:
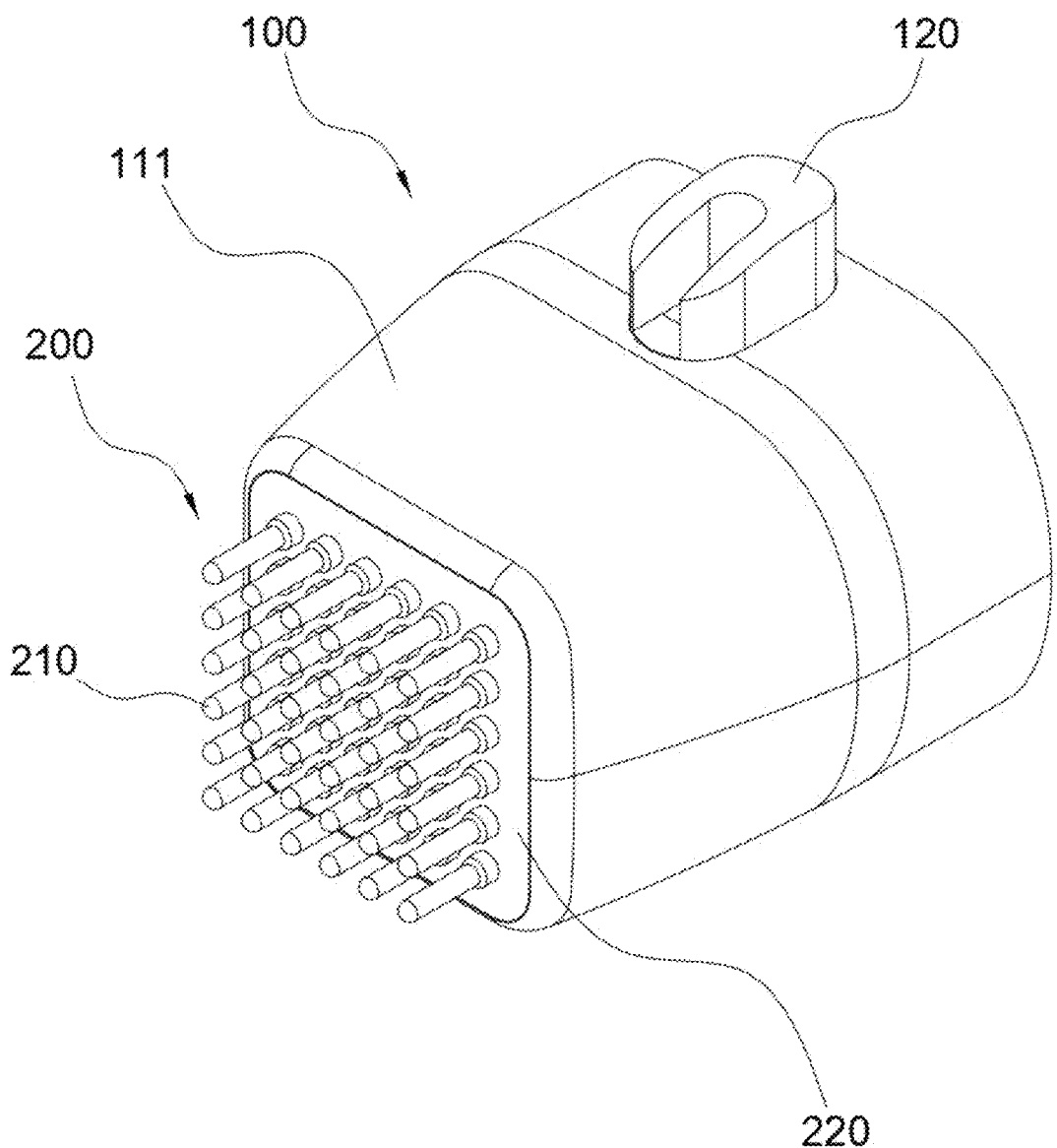
FIG. 1 illustrates a tip for use in a high-frequency skin treatment apparatus capable of uniform RF irradiation according to one embodiment.

Although the present invention can have various changes and modifications, specific embodiments will be illustrated in the drawings and described in detail herein.

However, this is not intended to limit the present disclosure to the specific embodiments, and it should be understood that the present disclosure includes all changes, equivalents, or substitutions included in the spirit and scope of the present disclosure. Similar components are denoted by similar reference numbers throughout the description of the drawings.

It will be understood that when a component is referred to as being "connected" or "coupled" to another component, the component may be directly connected or coupled to the other component or indirectly connected or coupled via intervening. On the other hand, when a component is referred to as being "directly connected" or "directly coupled" to another component, there are no intervening element present therebetween.

The terminology used herein is only used for the purpose of describing specific embodiments and is not intended to limit the present disclosure. Singular forms "a," "an" and "the" include plural forms unless the context clearly indicates otherwise. It will be further understood that terms "include", "have", etc. used herein designate the presence of features, integers, steps, operations, components, parts, or combinations thereof, but do not preclude a likelihood of the presence or addition of one or more other features, integers, steps, operations, components, parts, and/or combinations thereof.

Hereinafter, embodiments of the present invention will be described with reference to the accompanying drawings. The same reference numbers in the drawings indicate the same members. In describing the present invention, detailed description of related well-known functions or configurations will be omitted not to obscure the gist of the present invention.

The present invention relates to a tip for a high-frequency treatment apparatus in which non-invasive radio frequency (RF) irradiation is uniformly performed according to different curvatures of the skin for each person under treatment, and more particularly, to a tip for a high-frequency skin treatment apparatus capable of uniform RF irradiation, which allows contact pins for radiating a radio frequency signal to come into contact with skin regardless of the curvature of the skin and irradiate the skin with the RF signal so that each area is irradiated with a uniform radio frequency signal, thereby achieving skin treatment effects and solving problems caused by the skin curvature in an existing non-invasive RF irradiation method or apparatus.

An exemplary tip 1 for a treatment apparatus is mounted on a handpiece 2 connected to a high-frequency treatment apparatus to provide skin treatment and skin improvement to the person under treatment through a non-invasive RF irradiation method. The tip 1 includes a housing 100, a contact portion 200, and a driver 300. This will be described with reference to FIGS. 1 to 6.

When the tip 1 comes into close contact with a skin surface of the person under treatment, it may irradiate the skin surface with an RF signal, which is also referred to as a high frequency signal, in a non-invasive way. The RF signal flows into the skin, and generates heat inside the skin to cause coagulation and regeneration of the skin. The coagulation and regeneration results in skin treatment effects such as an enhancement of skin elasticity. Irradiation with an RF signal, hereinafter, refers to an irradiation with an RF signal through the tip 1 of a treatment apparatus according to the present invention.

Figure 2:
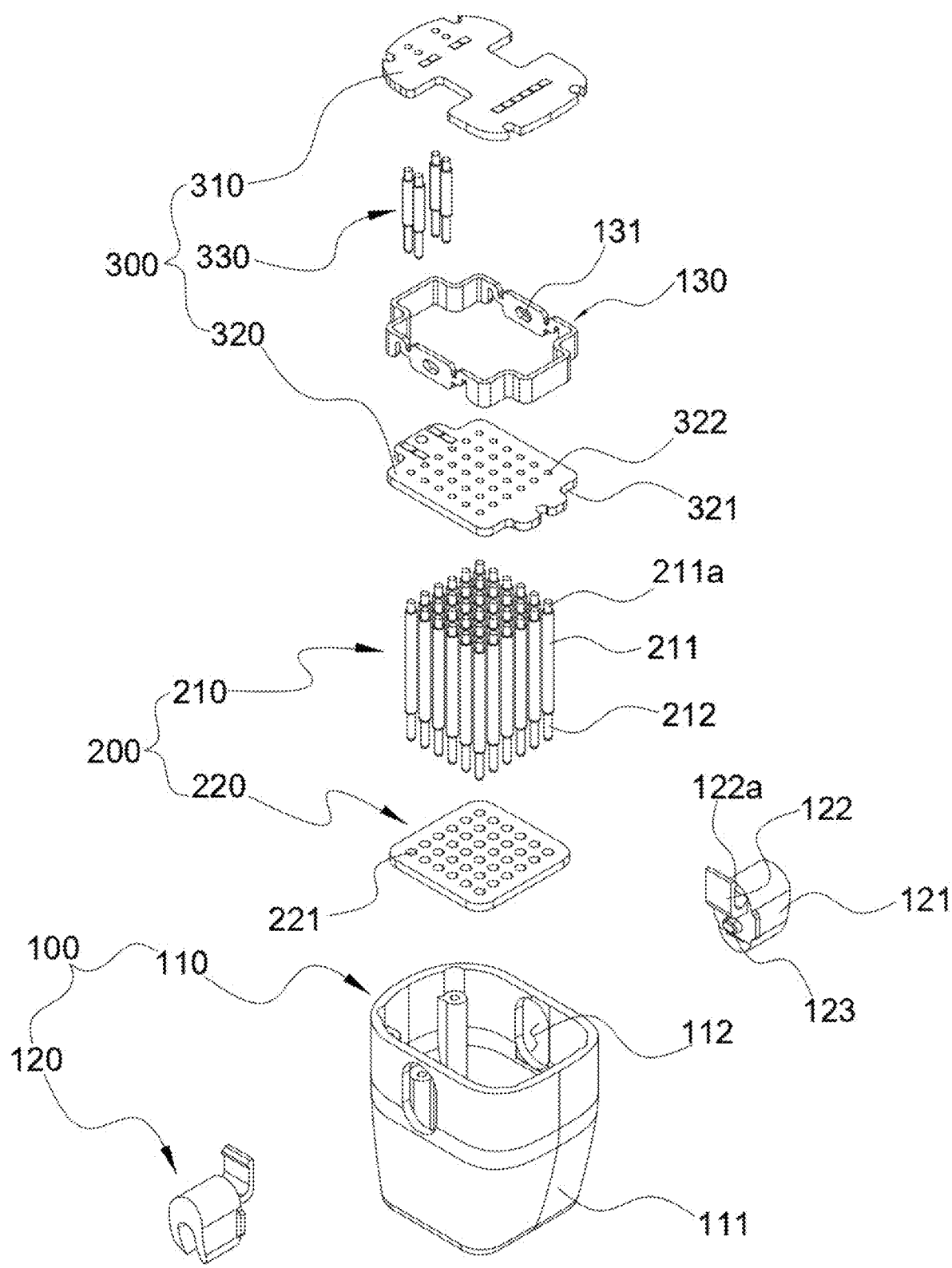
FIG. 2 is an exploded perspective view showing the tip for a high-frequency skin treatment apparatus capable of uniform RF irradiation according to an embodiment.
Figure 3:
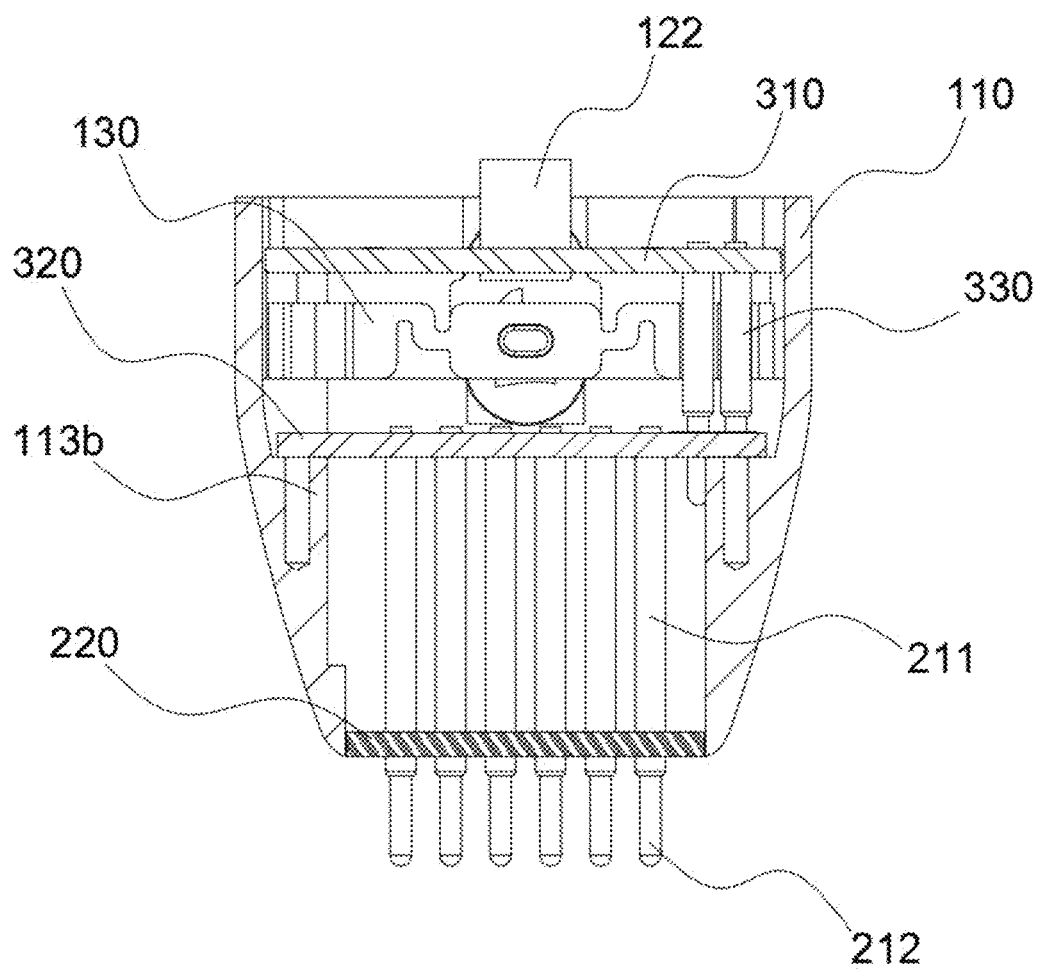
FIG. 3 represents a cross-sectional view of the tip for a high-frequency skin treatment apparatus capable of uniform RF irradiation according to one embodiment.
Figure 4:
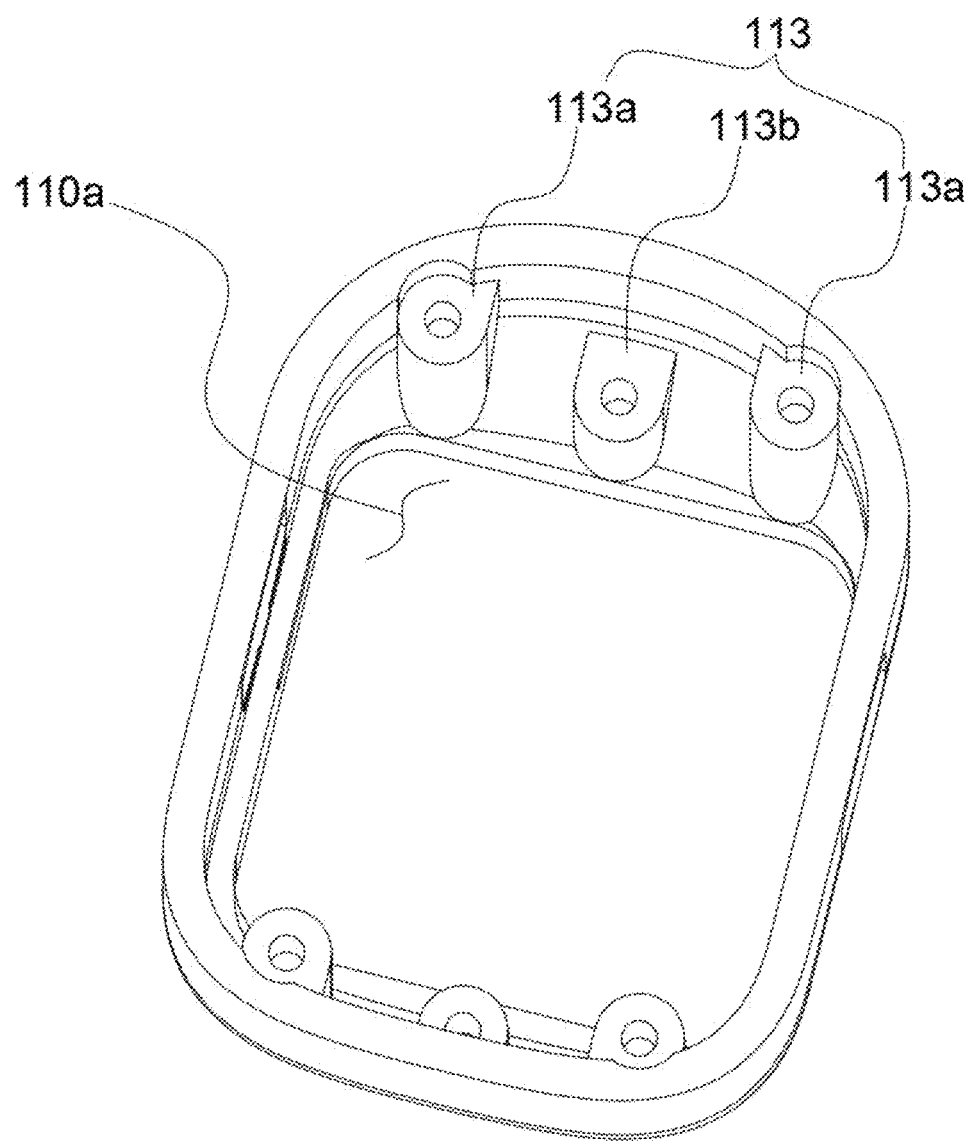
FIG. 4 depicts an upper perspective view of an outer frame according to an embodiment.
Figure 5:
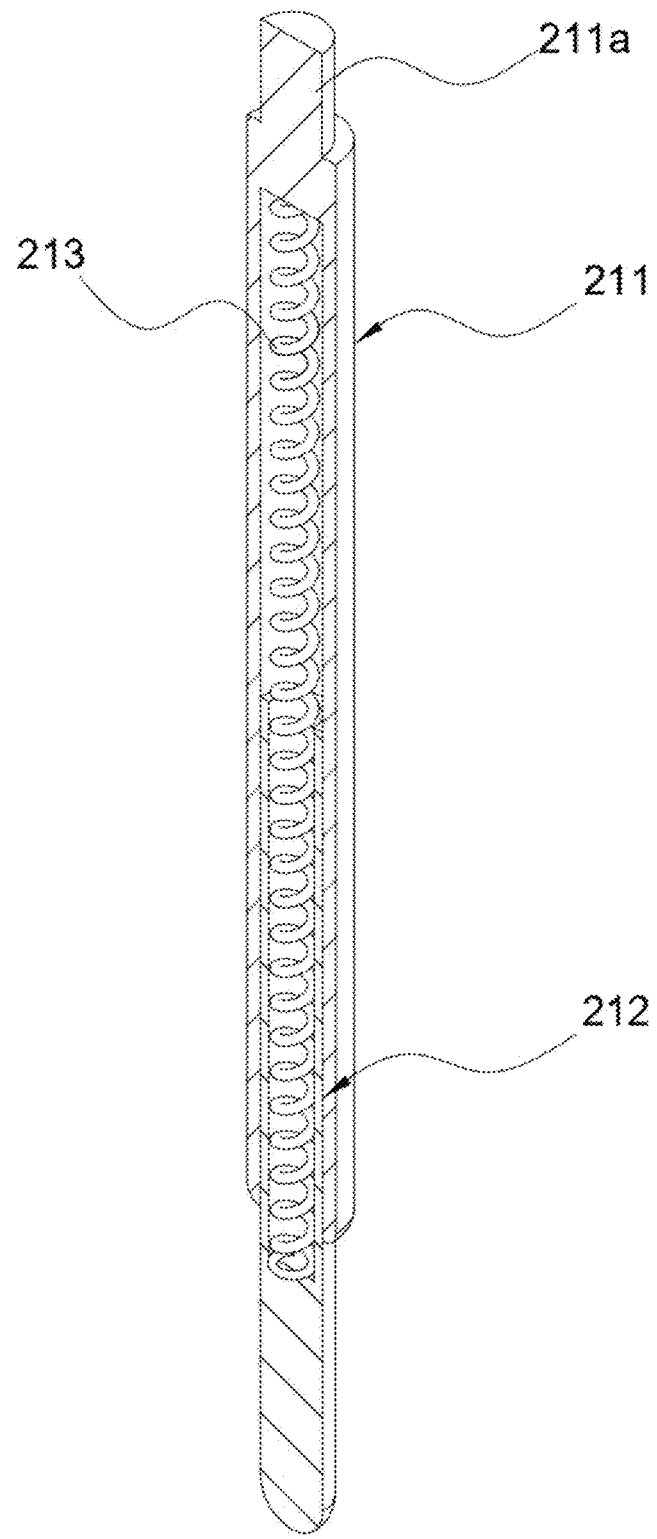
FIG. 5 shows a partial cross-sectional view of a contact pin according to one embodiment.
Figure 6:
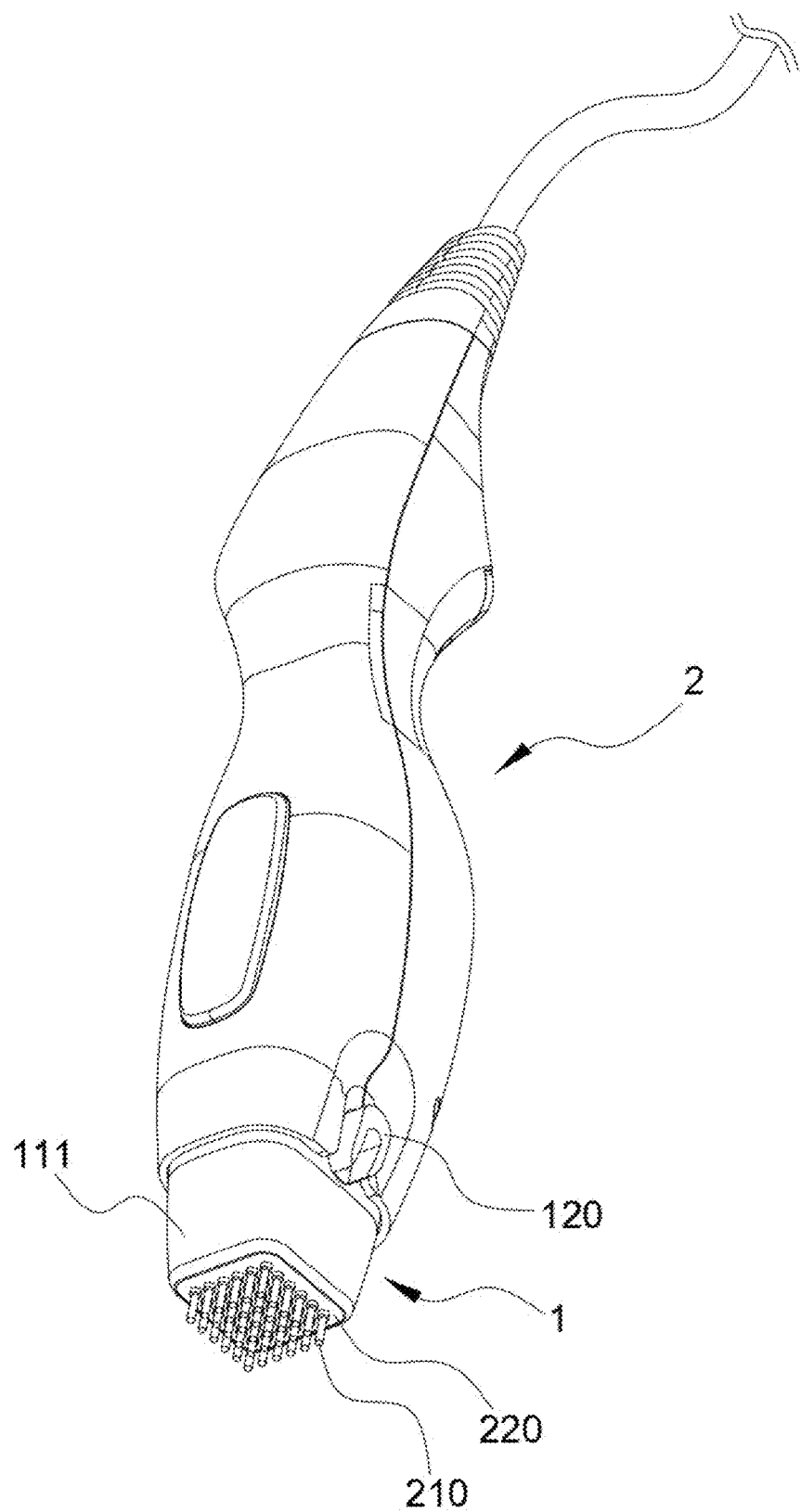
FIG. 6 describes an example in which a tip for a high-frequency skin treatment apparatus capable of uniform RF irradiation according to an embodiment is coupled to a handpiece.

FIG. 1 illustrates a tip for use in a high-frequency skin treatment apparatus capable of uniform RF irradiation according to one embodiment, FIG. 2 is an exploded perspective view showing the tip for a high-frequency skin treatment apparatus capable of uniform RF irradiation according to an embodiment, FIG. 3 represents a cross-sectional view of the tip for a high-frequency skin treatment apparatus capable of uniform RF irradiation according to one embodiment, FIG. 4 depicts an upper perspective view of an outer frame according to an embodiment, FIG. 5 shows a partial cross-sectional view of a contact pin according to one embodiment, and FIG. 6 describes an example in which a tip for a high-frequency skin treatment apparatus capable of uniform RF irradiation according to an embodiment is coupled to a handpiece.

The housing 100 is engaged to a coupling surface of the handpiece 2, and serves to protect the contact portion 200 and the driver 300, and the housing 100 comprises an outer frame 110 and an engagement member 120.

First, the outer frame 110 has a columnar shape with upper and lower ends, both being open. An inner space of the outer frame 110 accommodates the contact portion 200 and the driver 300. The upper end of the outer frame 110 is partially inserted into the coupling surface upon being coupled to the handpiece 2. At the lower end of the outer frame 110, the contact pins 210 of the contact portion 200 accommodated in the outer frame 110 protrude to a lower open surface 110*a*, which is an open surface at the lower side of the outer frame 110, and irradiate the skin of the person under treatment with a RF in a non-invasive way.

The outer frame 110 also has an inclined surface 111 whose dimension gradually decreases toward the lower side. When an upper end of the housing 100 is inserted into and coupled to the handpiece 2, the inclined surface 111 of the outer frame 110 may harmonize with the appearance of the handpiece 2 to fulfill an aesthetic feeling, and to facilitate focusing on an exact treatment area.

Figure 7:
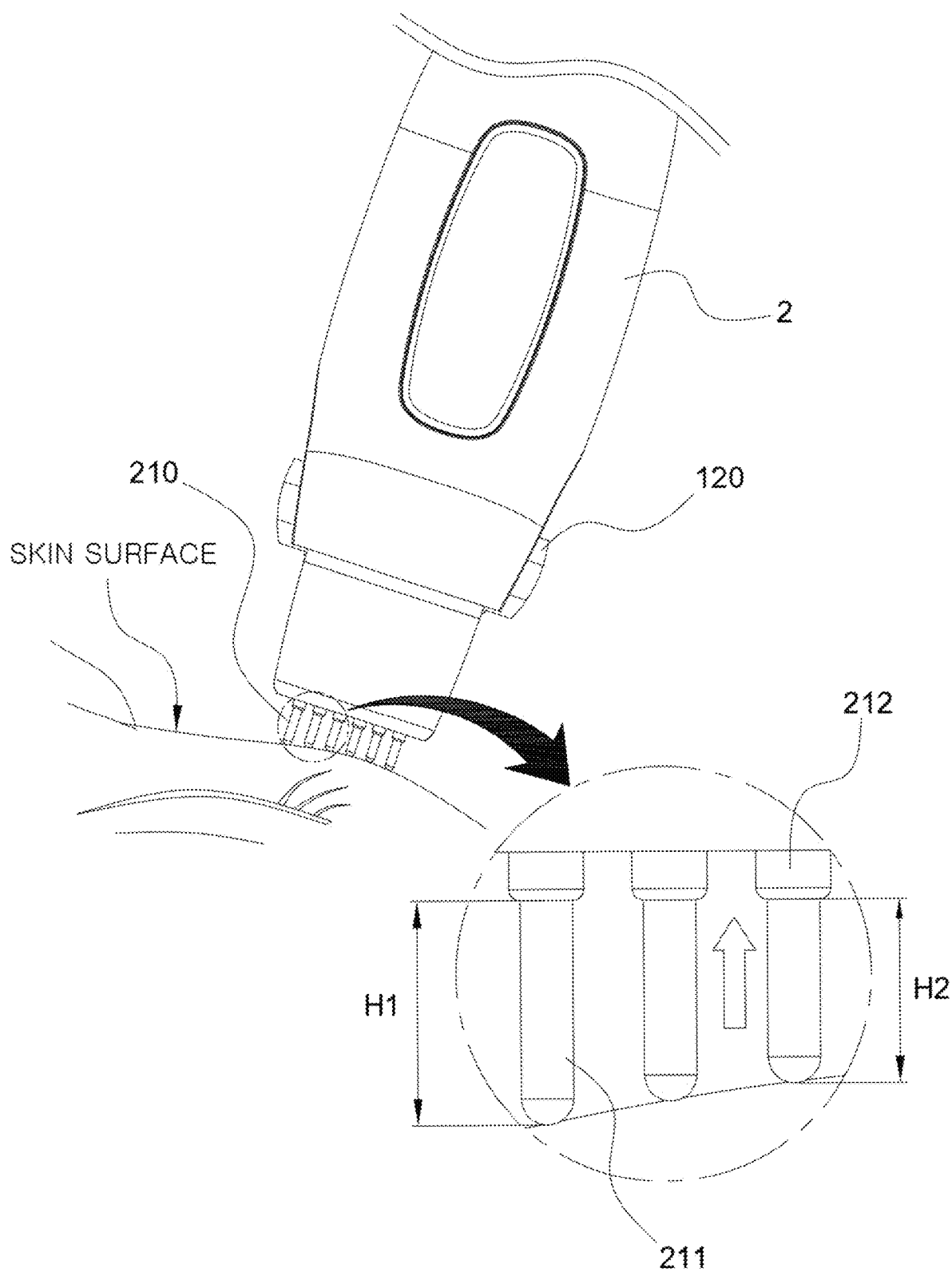
FIG. 7 demonstrates an example of a use of the tip for a high-frequency skin treatment apparatus capable of uniform RF irradiation according to one embodiment.
Figure 8:
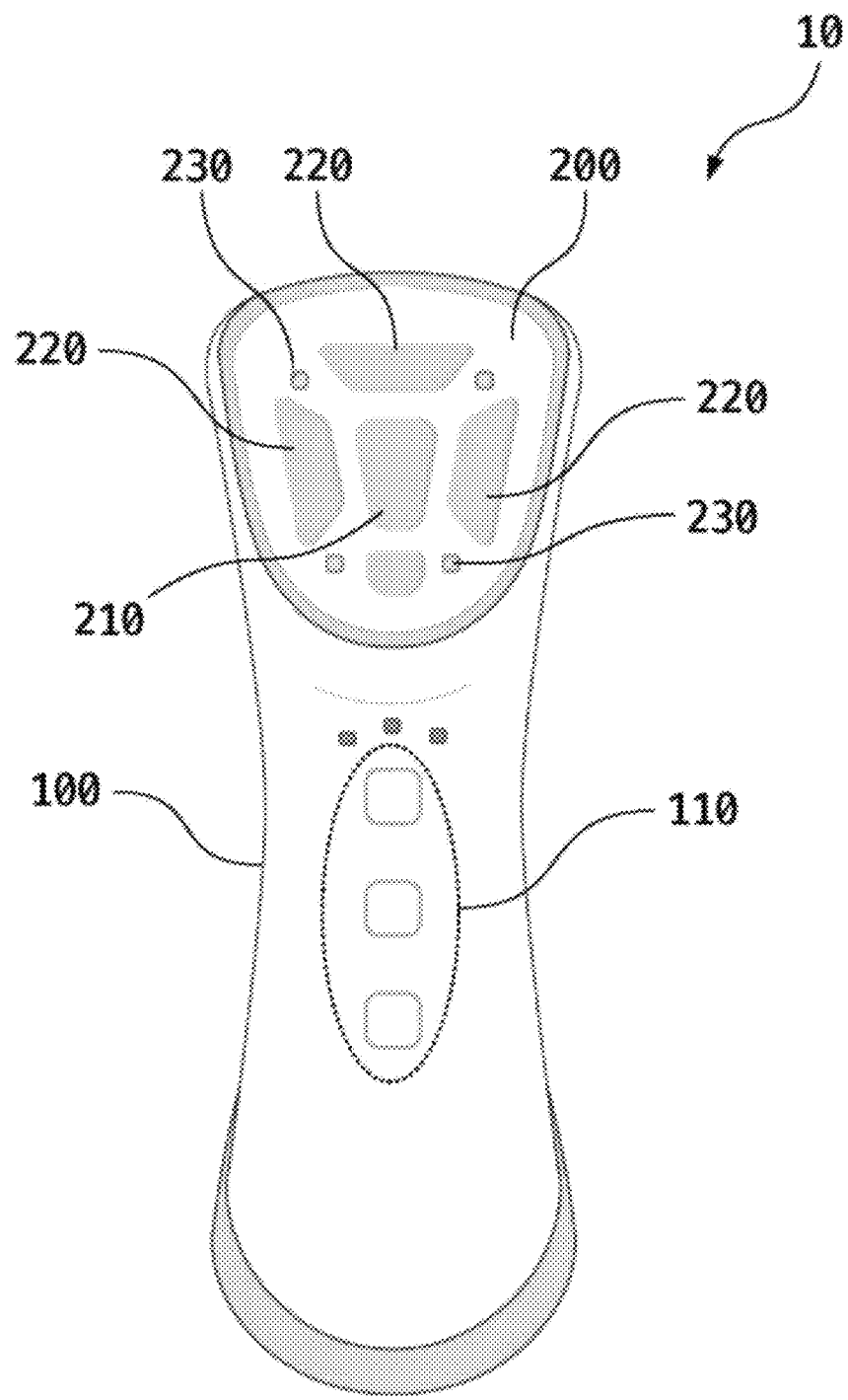
FIG. 8 illustrates an apparatus of prior art.

As illustrated in FIG. 7, only the inclined surface 111 and the contact portion 200 of the tip 1 coupled to the handpiece 2 protrude to from end of the handpiece 2 to the outside, thereby making it possible for the tip 1 to be inserted into and coupled to the handpiece 2 in a stable manner, and to reduce blind spots so that the operator can easily ascertain the positions of the contact pins 210 when an operator brings the contact portion 200 into close contact with the skin of the person under treatment. Moreover, it allows the contact pins 210 being effectively brought into close contact with the skin of a treatment area desired by the operator.

Further, an engagement hole 112 is formed on both sides of an upper end of the housing 100, and the engagement member 120 is inserted into and coupled to the engagement hole 112.

The engagement member 120 includes a hook 122, and the hook 122 passes through the engagement hole 112 so that it is coupled to the outer frame 110. The engagement hole 112 is formed by vertically perforating both sides of the upper end of the outer frame 110. The engagement member 120 further comprises a presser 121, and when one end of the engagement member 120 is inserted into the engagement hole 112 and coupled to the inside of the housing 100, the presser 121 protrudes to the outside while the hook 122 couples the engagement member 120 to the outer frame 110.

The operator may decouple the tip 1 from the handpiece 2 by pressing the presser 121. To be specific, when the operator presses the presser 121 to replace the tip 1, the presser 121 is pushed inward to be partially inserted into the outer frame 110. It is noted that a shape and size of the engagement hole 112 should correspond to a shape and size of the presser 121 so that the presser 121 can be inserted into the engagement hole 112 when the operator pushes the presser 121.

Meanwhile, the contact portion 200 and the driver 300 are provided inside the outer frame 110, and they are fastened therein, so that the contact portion 200 and the driver 300 can be fixed even and maintain their initial installation positions when the contract pins 210 are moving.

In particular, it is recommended to dispose a first PCB 310 and a second PCB 320 being spaced apart from each other. In an embodiment of the present invention, a mounting member 113 is formed along an inner surface of the outer frame 110 to maintain the contact portion 200 and the driver 300 on inner surface of the outer frame 110 in a coupling state.

The mounting member 113 may prevent an unintended movement or twist of the first PCB 310 and the second PCB 320 of the driver 300 in the outer frame 110. It also helps the first PCB and the second PCB maintaining an initial installation position in the outer frame 110 so that problems such as signal disconnection and breakdown due to external force even when the tip 1 for a treatment apparatus is frequently used.

This mounting member 113 can be divided into a first mounting member 113a and a second mounting member 113b as shown in FIG. 4. The first mounting member 113a extends longer than the second mounting member 113b, and is formed along the inner surface of the outer frame 110. The first mounting member 113a is provided on two inner sides, facing each other, of the outer frame 110, and it may comprises only one member for each side or a plurality of members.

The first PCB 310 is mounted on an upper end of the first mounting member 113a, and the first mounting member 113a prevents the first PCB 310 from falling downward. In particular, when the tip 1 is coupled to the handpiece 2, the coupling surface comes into contact with the first PCB 310 at the upper side and presses the first PCB 310, the first PCB 310 is supported by the first mounting member 113a at the lower side, so that the first PCB 310 can maintain a fixed state inside the tip 1.

Further, on the outer circumferential surface side, the first mounting member 113a is provided in A recessed groove 321 located at each corner of the second PCB 320, such that the second PCB 320 if prevented from moving or vibrating in a horizontal direction.

As illustrated in FIG. 3, the second PCB 320 may be mounted on an upper surface of the second mounting member 113b and supported thereby. Accordingly, the second mounting member 113b may prevent the second PCB 320 from falling. The second mounting member 113b can be installed at two inner sides, facing each other, of the outer frame 110 on which sides the first mounting members 113a are installed. The second mounting member may be provided between a pair of first mounting member 113a on the same inner side.

Therefore, the first PCB 310 and the second PCB 320 are supported by the first mounting member 113a and the second mounting member 113b so that the first PCB 310 and the second PCB 320 do not move downward while maintaining a predetermined distance therebetween. An engagement bracket t 130 may be provided between the first PCB and the second PCB. Since a failure or defect due to a collision of the first PCB 310 and the second PCB 320 can be prevented, signals can be stably transferred from the first PCB 310 to the second PCB 320 through a signal transfer pins 330.

Further, as the first PCB 310 and the second PCB 320 are manufactured based on dimensions and a shape of the inner space of the outer frame 110, and they are mounted on the mounting member 113 protruding inward from the outer frame 110, the first PCB 310 and the second PCB 320 do not deviate from initial installation positions, and do not move in a horizontal direction or twisting or vibrating in multiple directions. This structural feature may results in a stable RF irradiation without failure or configuration deviation.

In particular, considering that the second PCB 320 can be located an inner space of the outer frame 110 corresponding to the inclined surface 111, and it is difficult to precisely fit the shape of the second PCB 320 an inner shape corresponding to the inclined surface 111, the second PCB 320 can be manufactured to have a smaller dimension than the inner space of the outer frame 110. In an embodiment, the second PCB 320 is simply mounted on the second mounting member 113b, and the first mounting member 113a is inserted into the recessed groove 321, which is formed by recessing respective corners, thereby preventing the second PCB 320 from moving in a lateral (horizontal) direction as well as moving downward.

The engagement member 120 is coupled to the outer frame 110 so that the operator can attach and detach the tip 1 to or from the handpiece 2 by pressing the engagement member 120 when the handpiece 2 is coupled to the tip 1 later. The engagement member 120 includes a presser 121 where the operator presses to detach the tip 1, a hook 122 that inserts into the outer frame 110 for hooking and coupling thereto, and a fitting protrusion 123 that can be coupled with the outer frame 110 to improve a coupling force between the engagement member 120 and the outer frame 110.

The presser 121 is provided outside of the outer frame 110. When the presser 121 is pressed by the operator in order to couple (or separate) the tip 1 to (or from) the handpiece 2, the hook 122 connected to the presser 121 is then pushed inward of the outer frame 110, and the coupling between the hook 122 and the handpiece 2 is disengaged from the inside of the handpiece 2. Accordingly, the operator can easily separates the tip 1 from the handpiece 2.

The hook 122 has one end formed on the rear side of the presser 121, that is, a surface of the presser 121 corresponding to an outer surface of the outer frame 110, and the other end having a hook protrusion 122a which protrudes from the hook 122 toward the outer frame 110.

In an embodiment, the hook 122 has an elasticity, it extends from the back side of the presser, and it is vertically bent upward so that the other end can be hooked to the inner side of the handpiece 2.

Therefore, when the operator presses the presser 121, the hook 122 is moved in an inward direction of the tip 1, and the coupling between the hook protrusion 122a and the handpiece 2 is disengaged so that the tip 1 can be separated from the handpiece 2.

On the other hand, when the tip 1 is coupled to the coupling surface of the handpiece 2, the presser 121 is pressed similarly, an upper end of the hook 122 is located on the upper side of a hook jaw (not illustrated) formed separately on an edge of the coupling surface (not illustrated), and in this case, the hook protrusion 122a is hooked to the hook jaw of the handpiece 2 to be coupled and fixed.

Further, the handpiece 2 into which the tip 1 is inserted, has a groove communicating with the coupling surface. The groove is formed on a corresponding surface to a surface on which the engagement member 120 is located, so that the tip 1 can be easily coupled and fixed to the handpiece 2 due to the presser 121. The presser 121 is located on two sides at a lower end of the handpiece 2 when the tip is inserted into the handpiece 2.

On the other hand, when the presser 121 is connected only to the hook 122 and is included on the outside of the engagement hole 112, there is concern that the presser 121 can be easily separated or escape from the outer frame 110 due to an external force for pressing the presser 121 at various angles.

In particular, the presser 121, which is closeable, is included on the outside of the engagement hole 112, thereby preventing external dust or foreign substances from entering into the engagement hole 112. And when the presser 121 moves in a direction other than a pressing direction intended by a manufacturer, that is, a direction perpendicular to an inward direction from the outer surface of the outer frame 110, a gap is generated between the presser 121 and the engagement hole 112, and the hook 122 is also separated from the handpiece 2 so that the presser 121 itself can be separated from the housing 100.

Therefore, in the present invention, the fitting protrusion 123 protrudes on one surface of the presser 121 corresponding to the engagement hole 112, and the engagement bracket 130 fixed in close contact with the inner surface of the outer frame 110 and coupled to the presser 121 is included on the inner side of the outer frame 110 to prevent the presser 121 from being moved.

First, the fitting protrusion 123 protrudes from one surface of the presser 121, which is to be inserted in the outer frame 110, and is coupled to the engagement bracket 130 through the engagement hole 112.

The engagement bracket 130 is made of a material having elasticity and has a ring shape corresponding to the shape of the inner surface of the outer frame 110 so that an outer circumferential surface of the engagement bracket 130 can be clicked into the inner surface of the outer frame 110 in a close contact state.

In an embodiment, the engagement bracket 130 has a plurality of curvatures, which is different than the ring shape of the inner surface inclination or shape of the outer frame 110, the curvatures being formed in a horizontal direction. Due to the curvatures the presser 121 is pressed outward while the bent portion of the engagement bracket 130 contracts inward. The presser 121 maintains its initial state in which the presser 121 is provided outside the engagement hole 112 because of elastic restoring force of the engagement bracket 130 even under frequent pressure. And even when the presser 121 is pushed, the engagement bracket 130 is fixed in close contact with the inner surface of the outer frame 110, and only center portion on both sides of the engagement bracket 130 coupled to the presser 121 are moved inward by the pressing force so that the engagement bracket 130 does not deviate from an installation position.

Engagement member coupling grooves 131 fitted to the fitting protrusion 123 passing through the engagement hole 112 and inserted into the inside are formed at the center portions on both sides of the engagement bracket 130.

The engagement member coupling groove 131 is formed through perforation in the engagement bracket 130 to have the same shape and dimension with the fitting protrusion 123, so that the fitting protrusion 123 can be inserted into the engagement member coupling groove 131, to be fitted and fixed, allowing the engagement bracket 130 to fix the presser 121 at the outside of the engagement hole 112.

Therefore, the coupling between the fitting protrusion 123 and the engagement bracket 130 allows the engagement member 120 to be maintained in a state in which the engagement member 120 is coupled to the outer frame 110.

The contact portion 200 in which the lower end thereof partially protrudes from an open hole at a lower end of the housing 100 of the tip 1 comes into close contact with the skin of the person under treatment and irradiates the skin with the RF signal.

The contact portion 200 contacts closely with the skin of the person under treatment, and irradiates the skin with a high frequency signal, that is, an RF signal generated through the driver 300. The irradiation of RF generates deep heat in the skin, thereby promoting skin regeneration, and various skin improvement and treatment effects such as skin elasticity improvement and wrinkle treatment. This contact portion 200 may contacts with the skin in a non-invasive form, rather than penetrating the skin, and radiate radio frequencies.

The contact portion 200 may further include a plurality of contact pins 210, and a guide plate 220 that makes the contact pins 210 to be fixed in a state in which the contact pins 210 are mounted on a lower surface of the housing 100.

The contact pins 210 may correspond to an electrode in a tip for an RF irradiation treatment apparatus in the related art, and a plurality of contact pins 210 are disposed to be equally spaced apart around the lowermost surface of the tip 1. In this case, as illustrated in FIG. 1, a total of 36 contact pins 210 are equally spaced apart from each other in longitudinal and lateral directions, six contact pins 210 each in the longitudinal and lateral directions.

Please be noted that, although only one embodiment is represented herein, the number of pins, spacing, arrangement shape, or the like of the contact pins can be designed and manufactured in various ways.

The contact pins 210 receive the RF signal generated through the driver 300 provided in the housing 100 and irradiate the skin with the RF signal.

Figure 9:
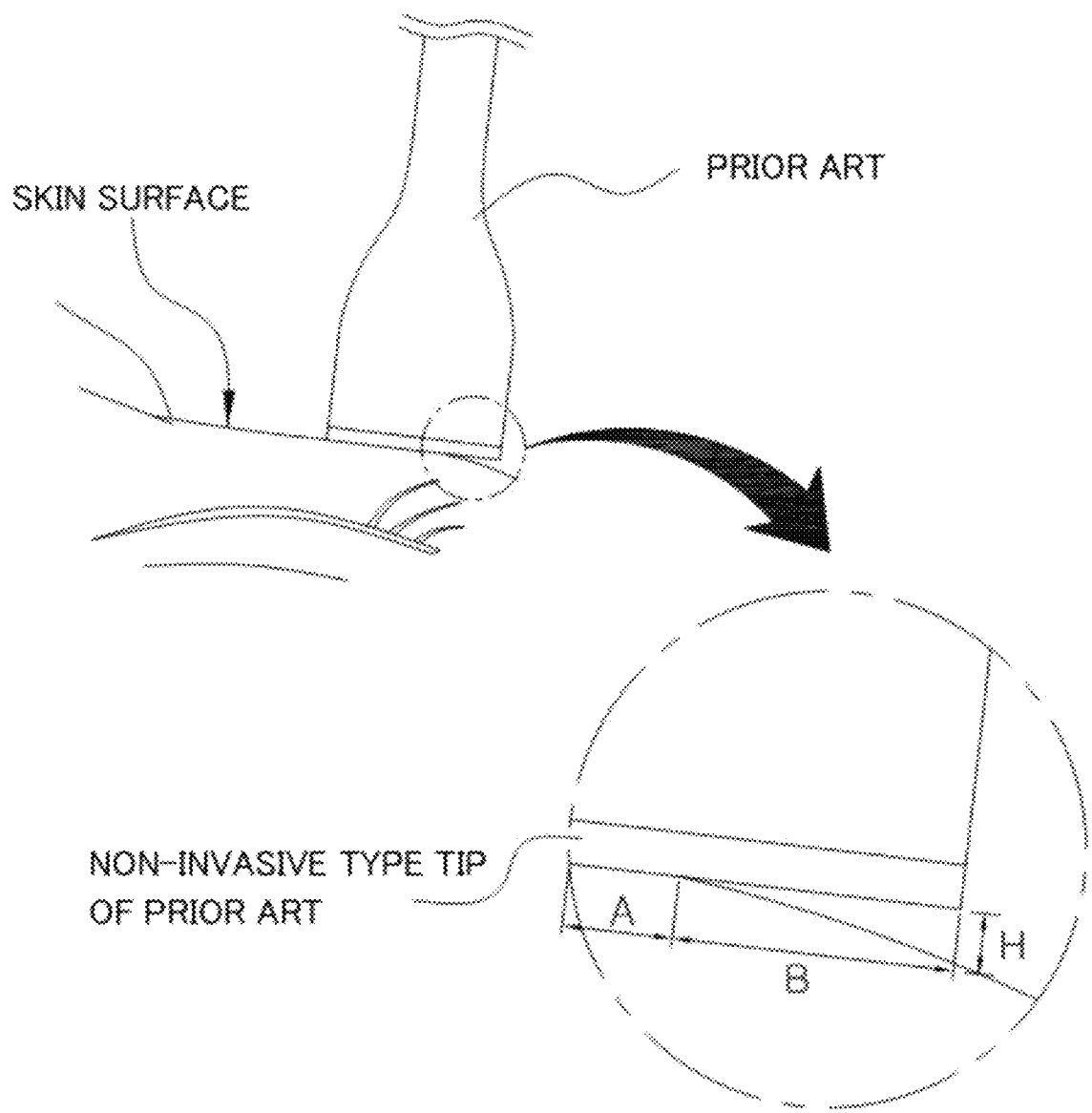
FIG. 9 is an illustrative diagram explaining problems that may occur in an apparatus of prior art.

On the other hand, with an electrode capable of non-invasive treatment having a flat surface or a curved surface, a high-frequency focusing depth of the RF irradiation can be different depending on the curvature of the skin as illustrated in FIG. 9. Accordingly, when the skin is irradiated with the signal at an unintentional focusing depth, desired skin RF treatment effects may not be obtained, or the person under treatment may feel excessive heat or burn in severe cases.

Therefore, in the present invention, a plurality of contact pins 210 are provided, and as each pin has elastic restoring force, lengths of the contact pins 210 may vary according to a curvature (inclination) of the skin with which the tip 1 comes into contact. As a result, every contact pins 210 may come into close contact with a corresponding area of the skin, and thus the focusing depth of the skin will become uniform.

The contact pins 210 have the elastic restoring force and include a fixed frame 211, a movable frame 212, and an elastic body 213 to irradiate the skin with the radio frequencies. First, the fixed frame 211 is coupled and fixed to the housing 100 so that the respective contact pins 210 are spaced apart from each other at equal intervals in a longitudinal direction and fixed. The fixed frame 211 is fixed not to deviate from an initial installation position, unlike the movable frame 212 that moves according to the curvature of the skin of the operator at the time of the treatment using the tip 1 for a treatment apparatus, so that the contact pins 210 can maintain their respective positions even when a vibration or impact is delivered from the movement of the movable frame 212.

The fixed frame has a cylindrical fitting member 211a which protrudes at an upper end of the fixed frame 211, and have smaller diameter than an outer diameter of the fixed frame 211. This fitting member 211a passes through and is coupled to the second PCB 320 to be described below, and ultrasonic waves generated from the second PCB 320 are transmitted to the movable frame 212 through the fixed frame 211 and finally transferred to the skin of the operator.

In particular, since the fixed frame 211 is firmly coupled to the second PCB 320 together with the guide plate 220, to be described below, the contact pins 210 can be stably coupled to the housing 100 and receive a control signal and ultrasonic waves from the driver 300, and operates without a defect.

In an embodiment, a fitting hole 322 for coupling to the fixed frame 211 is formed through perforation in the second PCB 320, and the fitting hole 322 has the same shape and inner diameter as an upper end of the fitting member 211a so that the fitting member 211a can be stably fitted into the fitting hole 322.

A lower surface of the fixed frame 211 is opened, and the movable frame 212 is inserted through the opened lower surface and moves along the inner side of the fixed frame 211 in a vertical direction.

The movable frame 212 has the same shape as the fixed frame 211, and has the same diameter as the lower open surface of the fixed frame 211. A lower end of the movable frame 212 partially protrudes from the lower surface of the fixed frame 211. When the lower end comes into contact with the skin due to the non-invasive irradiation manner, the movable frame 212 may be forced to be inserted into the fixed frame 211, total lengths of the contact pins 210 are reduced so that the contact pins 210 come into close contact with the skin surface.

Meanwhile, when the movable frame 212 comes into close contact with the skin in a treatment process for a non-invasive irradiation manner as described above and be pushed up to be inserted into the fixed frame 211, it needs to return to an original position for reuse. Therefore, the elastic body 213 having an elastic restoring force is included inside the contact pin 210 so that a degree of movement of the movable frame 212 is adjusted according to the magnitude of the pressing force applied to the movable frame 212 and the total length of the contact pin 210 can be adjusted.

An upper end of the elastic body 213 is fixed to an upper inner surface of the fixed frame 211, a lower end thereof is fixed to an inner lower surface of the movable frame 212. The movable frame 212 protrudes to the outer side of the fixed frame 211 or is inserted into the inside according to compression or extension of the elastic body 213 so that a total length of the entire contact pin 210 is adjusted.

The elastic body 213 can be most preferably a spring as illustrated in FIG. 5, but the present invention is not limited thereto. The elastic body 213 is compressed due to a pressing force when the movable frame 212 is pressed from the outside (that is, when the elastic body 213 comes into close contact with the skin for non-invasive irradiation) so that the connected movable frame 212 is inserted into the fixed frame 211, and when there is no pressing force, the movable frame 212 may protrude to the lower side of the fixed frame 211 again due to the elastic restoring force of the elastic body 213.

In the embodiment, although the movable frame 212 moves through the lower open surface of the fixed frame 211, as the elastic body 213 connects the movable frame 212 and the fixed frame 211, the movable frame 212 is not completely drawn out of the fixed frame 211. The end of the movable frame 212 is connected to the elastic body in a state of a part of which being inserted into the fixed frame 211 so that the end of the movable frame 212 is not drawn out of the fixed frame 211, and the movable frame 212 is inserted into the fixed frame 211 when the elastic body 213 is compressed.

That is, when the tip 1 coupled to the handpiece 2 is brought into a skin surface, e.g., a face surface, and the skin surface is irradiated with the RF signal in a non-invasive way as illustrated in FIG. 7, the movable frame 212 is inserted into the fixed frame 211 according to the curvature of the treatment area with which each contact pin 210 comes into contact. When placed on the same horizontal line as in a partially enlarged view, all the plurality of contact pins 210 come into close contact with the skin surface, and a height H1 of the contact pin 210 in a lower portion of the skin surface and a height H2 of the contact pin 210 in a highest portion of the skin surface protruding outward are automatically adjusted according to the skin surface.

Therefore, in the case of the contact pins 210 having the above-described configuration, the lengths of the contact pins 210 coming into close contact with the skin are adjusted according to the curvature and height of the skin. To be specific, the tip 1 may be pressed until a contact pin 210 which corresponds to a farmost area of skin comes into close contact therewith, and at that time, remaining contact pins 210 are compressed accordingly. As all the contact pins 210 equally come into close contact with the skin within a range to be irradiated with an RF signal using the tip 1 for a treatment apparatus, and the skin is irradiated with the RF signal with the same focusing depth, the skin can be irradiated with a uniform amount of RF signal. In particular, since there is no spacing between the contact portion 200 performing the non-invasive RF irradiation and the skin surface, the RF signal is not radiated to an unintended area and depth, and problems such as burn do not occur.

The guide plate 220 covers the lower open surface of the housing 100 and it fixes and guides the plurality of contact pins 210 so that the lengths of the contact pins 210 are adjusted at designated positions.

The guide plate 220 is configured to be a plate having the similar shape as an inner surface at the lower end of the housing 100, and the guide plate 220 comprises through holes 221 through which the contact pins 210 pass. The through holes 221 are configured to be spaced apart from each other at regular intervals, and has an inner diameter which is equal to the outer diameter of the fixed frame 211 of the contact pins 210. An outer surface of a lower end of the fixed frame 211 is inserted into and fixed to the through-hole 221 so that the fixed frame 211 is coupled to the guide plate 220. A part of the outer lower end of the fixed frame 211 and the movable frame 212 protrude outside the guide plate 220, making it possible to easily perform a treatment in a non-invasive irradiation manner through the tip 1 for a treatment apparatus.

If the apparatus is frequently used or there is a collision, an external force may be transferred from the movable frame 212, such that the contact pins 210 may deviate from initially installed positions due to an elastic movement of the elastic body 213. In the embodiment, the guide plate 220 fixes the contact pins 210 in a state in which the contact pins 210 are spaced apart from each other at regular intervals and disperses an external force received by the contact pins 210 in order to prevent the external force from being applied to the other contact pins 210 so that the plurality of contact pins 210 are able to operate while maintaining their initial arrangement.

The above described contact portion 200 allows a uniform treatment with a uniform focusing depth and RF irradiation amount, which cannot be achieved by using a tip performing a non-invasive irradiation manner in the related art. It further results in even skin treatment effects in the entire treatment area, and preventing problems such as soreness, burns, lacerations, and tanning in the treatment area due to an unintentional focusing depth.

The driver 300 receives power and a control signal from the handpiece 2 when the tip 1 for a treatment apparatus is connected to the handpiece 2, and operates the contact portion 200 according to a command.

The driver 300 includes the first PCB 310 that is connected to the handpiece 2 to receive power and a control signal and control the operation of the tip 1. The second PCB 320, that the plurality of contact pins 210 pass through and are coupled to, receives a control signal from the first PCB 310 to generate a high frequency signal, and transfers the high frequency signal to the connected contact pins 210. The driver 300 further comprises a signal transfer pin 330 that connects the first PCB 310 to the second PCB 320 and transfers a control signal therebetween.

When the housing 100 of the tip 1 is coupled to the handpiece 2, the first PCB 310 is connected to a power supply of the handpiece 2 and receives power from the handpiece 2 so that the first PCB 310 can be operated. In an embodiment, when the tip 1 is attached to the handpiece 2, the first PCB 310 may be connected to components of the handpiece 2 so that the first PCB 310 may receive the power and the control signal.

When the operator manipulates the handpiece 2 or the treatment apparatus, the first PCB 310 may control an amount of high frequency signal radiated to the tip 1, operating mode, or the like according to a received control signal, and send a corresponding control signal to the second PCB 320.

The second PCB 320 may receive a control signal for operation from the first PCB 310 via the signal transfer pin 330, and transfer the high frequency signal to the plurality of connected contact pins 210 according to the signal.

First, the second PCB 320 comprises fitting holes 322 to which the plurality of contact pins 210 can be coupled are, similar to the guide plate 220. The inner diameter of the fitting hole 322 is similar with an outer diameter of the fitting member 211a, so that the fitting member 211a can be fitted into the fitting hole 322 and the upper end of the contact pin 210 can be fitted and fixed to the second PCB 320.

In an embodiment, the outer diameter of the fitting member 211a is smaller than the outer diameter of the fixed frame 211, so that a step is formed at an upper end of the fixed frame 211. The second PCB 320 may be hooked to the upper end of the fixed frame 211 such that the upper end of the contact pins 210 may be mounted on the second PCB 320.

Further, the fitting holes 322 are formed on the same vertical line as the through-holes 322 formed in the guide plate 220, and the arrangement of the fitting holes 322 corresponds to that of the contact pins 210. Thus, the upper and lower ends of the contact pins 210 pass through and are coupled to the second PCB 320 and the guide plate 220, respectively.

Therefore, the plurality of contact pins 210 coupled to the second PCB 320 through the fitting member 211a receive the high frequency signal generated from the second PCB 320, and radiate RF to the skin.

Further, as described above, the second PCB 320 comprises the recessed groove 321 which is coupled to and fixed by the first mounting member 113a so that the second PCB 320 can maintain its initial installation position even when the movable frame 212 is strongly compressed on the lower side and the tension is delivered to the fixed frame 211.

The signal transfer pin 330 may connect the first PCB 310 and the second PCB 320 which are provided to be spaced apart from each other in a vertical direction inside the housing 100, and transfer a signal of the first PCB 310 to the second PCB 320. That is, the first and second PCBs 310 and 320 can be easily transfer drive control signals through the signal transfer pin 330, and a problem such as signal failure due to twisting or damage of internal cables can be minimized.

Further, since the signal transfer pin 330 supports and fixes the first and second PCBs 310 and 320 so that the first and second PCBs 310 and 320 are maintained to be spaced apart in the vertical direction, and the first and second PCBs 310 and 320 may be fixed while maintaining initial installation positions inside the housing 100 even if the apparatus is frequently used or there is an external collision. In particular, in an embodiment, the first PCB 310 or the second PCB 320 stably maintain their contact with each other inside the housing 100. A handpiece of a prior art, which includes a tip, may experience signal failure when the operator moves the coupled tip in different angles and directions using the handpiece.

Therefore, in an embodiment of the present invention, the signal transfer pin 330 allows the first and second PCBs 310 and 320 being electrically connected and maintaining their position inside the housing 100 in a state of being spaced apart from each other.

The tip 1, as described above, is coupled to one end of the handpiece 2 which is connected to the skin treatment apparatus, and the plurality of contact pins 210 provided in the tip 1 come into close contact with the skin surface of the person under treatment. Accordingly, the person under treatment may obtain skin treatment effects such as collagen regeneration through RF irradiation, as illustrated in FIGS. 6 and 7.

Further, the driver 300 receives a control signal which is generated according to a manipulation of the operator through the handpiece 2 and a main body of the skin treatment apparatus connected to the handpiece 2, and transfers the control signal to the plurality of contact pins 210, so that the treatment area, i.e., an area under an RF irradiation influence range of the tip 1, may receive a uniform amount of RF irradiation, thereby improved effects such as uniform skin treatment and skin improvement can be obtained.

Meanwhile, the above-described tip 1 may further include a control unit (not drawn).

The control unit controls the driver 300 so that the uniform amount of the RF signal can be radiated from each contact pin 210. The control unit can control the driver 300 so that the RF is radiated only when all the contact pins 210 are brought into close contact with the skin surface of the person under treatment during the treatment, or so that an amount of the RF signal radiated from each contact pin 210 can be identified and calculated in order to ensure that the uniform amount of the RF signal is radiated with an accuracy.

Meanwhile, the handpiece tip 1 for a high-frequency skin treatment apparatus has been described in the present specification, but the present invention is not limited to the high-frequency skin treatment apparatus, and can be applied to handpieces of various apparatuses such as skin treatment apparatuses or skin stimulators capable of performing skin treatment and the like by way of irradiating with an RF signal, ultrasonic waves, or the like in a non-invasive way.

The embodiments disclosed in the drawings and specifications are merely preferred exemplary ones. The terms recited herein are only used for the purpose of describing the present invention and are not used to limit the meaning or the scope of the present invention described in claims. Therefore, those skilled in the art will understand that various modifications and equivalents are possible therefrom. Please be noted that the technical protection scope of the present invention should be determined by the technical spirit of the claims appended hereto.

The invention claimed is:

1. A tip for a high-frequency skin treatment apparatus irradiating uniform radio frequency (RF), the tip being coupled to a handpiece to radiate a radio frequency (RF) signal to a human body in a non-invasive way, and comprising:
    a housing;
    a contact portion coupled to the housing and comprising a plurality of contact pins that are configured to come into close contact with skin of the human body to irradiate the skin with the RF signal; and
    a driver configured to drive the contact portion so that the contact portion radiates the RF signal according to a control signal transferred from the handpiece,
    wherein each of the contact pins comprises:
    a fixed frame, an upper end of which is inserted into the housing and fixed thereto;
    a moving frame coupled to the fixed frame such that the moving frame is inserted into the fixed frame from a lower end of the fixed frame, the moving frame moving in a vertical direction; and
    an elastic body provided inside the fixed frame and the moving frame, to be compressed or extended according to an external force received by the moving frame to thereby move the moving frame, and
    the elastic body connects an upper inner surface of the fixed frame to an upper inner surface of the moving frame to prevent the moving frame from deviating from the lower end of the fixed frame,
    wherein the driver comprises:
    a first PCB connected to the handpiece and configured to receive the control signal;
    a second PCB provided below the first PCB and connected to the contact pins; and
    signal transfer pins having two opposing ends, the two opposing ends respectively passing through the first PCB and the second PCB, to communicate signals between the first PCB and the second PCB,
    wherein the signal transfer pins support the first and the second PCBs such that the first and the second PCBs are maintained to be spaced apart from each other; and
    wherein a fitting member, which passes through the second PCB and is fitted and fixed thereto, is formed at the upper end of the fixed frame, the second PCB comprises fitting holes therein, the fitting holes being formed by perforation and having the same diameter as the outer diameter of the fitting member, and the number of the fitting holes is equal to the number of the plurality of contact pins, and the fitting holes are spaced apart from each other at regular intervals in vertical and horizontal directions in the second PCB.

2. The tip for a high-frequency skin treatment apparatus irradiating uniform radio frequency (RF) according to claim 1, wherein the housing comprises:
    an outer frame;
    engagement members, each of which is disposed at two opposing sides of the outer frame, so as to engage and fix the outer frame to the handpiece; and
    engagement holes, each of which is formed at said two opposing sides of the outer frame, such that the engagement members are inserted into the engagement holes and coupled and fixed thereto.

3. The tip for a high-frequency skin treatment apparatus irradiating uniform radio frequency (RF) according to claim 2, wherein the housing further comprises an engagement bracket, and
    the engagement bracket is installed into the outer frame and is coupled to one end of each of the engagement members inserted into the outer frame, such that the engagement members protrude outside of the outer frame in a state in which the engagement members are coupled to the engagement bracket.

4. The tip for a high-frequency skin treatment apparatus irradiating uniform radio frequency (RF) according to claim 2, wherein the contact portion further comprises a guide plate configured to close an open lower surface of the outer frame and being coupled to the contact pins,
    the guide plate comprises a plurality of through-holes therein, the through-holes being formed by perforation and being spaced apart from each other in vertical and horizontal directions at regular intervals, and the plurality of contact pins passing through the through-holes, and
    an inner diameter of the through-holes is equal to an outer diameter of the contact pins, so that the contact pins pass through the through-holes to be inserted and fixed.

5. The tip for a high-frequency skin treatment apparatus irradiating uniform radio frequency (RF) according to claim 2, wherein a mounting member is formed on an inner surface of the outer frame, and the mounting member comprises a first mounting member extending downward along the inner surface of the outer frame so that an upper end of the first mounting member is disposed on a same horizontal line as a lower surface of the first PCB, and a second mounting member extending downward along the inner surface of the outer frame so that an upper end of the second mounting member is disposed on a same horizontal line as a lower surface of the second PCB, and
    the upper end of the first mounting member comes into close contact with the lower surface of the first PCB to further support the first PCB, and the upper end of the second mounting member comes into close contact with the lower surface of the second PCB to further support the second PCB.

6. The tip for a high-frequency skin treatment apparatus irradiating uniform radio frequency (RF) according to claim 1, wherein the elastic body has a spring shape with an elastic restoring force.

* * * * *